US00PP09287P

United States Patent [19]

Hofmann

[11] Patent Number: Plant 9,287

[45] Date of Patent: Sep. 12, 1995

[54] VARIETY OF GERANIUM NAMED 'L'AMOUR'

[75] Inventor: Christa Hofmann, Grossdittmannsdorf, Germany

[73] Assignee: Oglevee, Ltd., Connellsville, Pa.

[21] Appl. No.: 334,852

[22] Filed: Nov. 1, 1994

[51] Int. Cl.[6] ..... A01H 5/00
[52] U.S. Cl. ..... Plt./87.12
[58] Field of Search ..... Plt. 87.12

[56] References Cited

PUBLICATIONS

Cairol, D., et al., (1979) "Les Cultivars de Pelargonium de Semis" *Horticulture Francaise,* vol. 103, pp. 7–14.

*Primary Examiner*—James R. Feyrer
*Attorney, Agent, or Firm*—Webb Ziesenheim Bruening Logsdon Orkin & Hanson

[57] ABSTRACT

This new cultivar is characterized by its pale pink florets accented with a dark pink eye against a medium green foliage. The new cultivar is easily rooted and has a compact mound habit, basal branching and free and early flowering.

1 Drawing Sheet

BACKGROUND OF THE INVENTION

The present invention comprises a new and distinct cultivar of *Pelargonium*×*hortorum* known by the varietal name 'L'amour' (Oglevee No. 2021, Breeder No. P-453). This variety will be commercialized under the name Love Song. The new variety was discovered in a selected breeding program in Dresden, Germany in May of 1990. The new variety is a selection from the crossing of a combination of several inbred breeding-lines which are unidentified but maintained as proprietary for breeding purposes. The new variety was first asexually reproduced by cuttings at Dresden, Germany in September of 1990. The new variety has been asexually reproduced by cuttings at Oglevee, Ltd. in Connellsville, Pa. over a two year period starting Apr. 1, 1992. It has also been trial and field tested at Connellsville and has been found to retain its distinctive characteristics through successive propagations.

The cultivar, when grown in a glass greenhouse in Connellsville, Pa. using natural light and 60° F. night and 72° F. day, has a response time of six weeks from a rotted cutting to flowering in a 10 cm pot. The response time was determined on plants grown in soilless media employing constant fertilizer 200 parts per million of nitrogen and potassium in full light. The rooted cuttings were potted on Feb. 23, 1994 and flowered on Apr. 7, 1994.

DESCRIPTION OF THE DRAWING

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee, Ltd. in Connellsville, Pa. The plant history was taken on six week plants in a 15 cm pot blossomed under natural light in a greenhouse and the color readings were taken indoors under 200–220 foot candles of fluorescent cool white light.

Color references are primarily to the RHS Color Chart of the Royal Horticultural Society of London.

THE PLANT

Classification:
- *Botanical.*—*Pelargonium*×*hortorum.*
- *Commercial.*—Zonal florists' geranium.

Form: Compact mound form.
- *Height.*—15.0–18.0 cm from media surface.
- *Growth.*—Compact, semi-dwarf; free flowering, free branching with semi-double flowers.

Strength: Stands upright without artificial support.
Foliage: Stalked leaf attachment.
Leaves:
- *Size.*—8.0–8.5 cm across; fully expanded leaf.
- *Shape.*—Reniform; cordate base.
- *Margin.*—Crenate.
- *Texture.*—Slightly pubescent.
- *Color.*—Top: Green Group 137A. Bottom: Green Group 137C.
- *Zone.*—No zone present.
- *Ribs and veins.*—Venation: Palmate. Color: Yellow-Green Group 146C.

Petioles:
- *Color.*—Yellow-Green Group 146C.
- *Length.*—5.5–6.5 cm.

Stem:
- *Color.*—Yellow-Green Group 146C.
- *Internodes.*—2.5–4.0 cm in length.

THE BUD

Shape: Upright hemispherical cluster.
Size: 2.5–3.5 cm across.

INFLORESCENCE

Blooming habit: Semi-double; slow to shatter; free and early flowering.
Size: Fully Open Bloom: 9.0–11.0 cm.
Borne: Umbel; florets on pedicel; pedicel on peduncle; 14.0–17.0 cm above foliage.
Open florets:
- *Form.*—Slightly cupped; semi-double.
- *Color.*—Top: Red-Purple Group 65C. Bottom: Red Group 56D. Eye: Red-Purple Group 57D.

*Petals.*—Separate, not united; margin entire; obovate; smooth, flat to slightly cupped; 6–8 in number.

*Size.*—4.3–5.0 cm across.

Closed florets:

*Bud size.*—1.2–1.3 cm.

*Color.*—Shows only faintest hint of color.

Texture and Appearance: Smooth; Appearance from a distance is a light pink flower with a distinct dark pink eye above medium green foliage.

Petaloids:

*Quantity.*—0–3.

*Shape.*—Single base with ends split to three points; points twisted.

*Color.*—Top: Red-Purple Group 65C. Bottom: Red Group 56D.

Pedicel:

*Length.*—1.8–2.1 cm.

*Color.*—Base (peduncle end): Yellow-Green Group 146D. Tip (stipule end): Red-Purple Group 59B.

Peduncle: 19.5–24.0 cm in length. Arises from the node opposite the leaf petiole.

*Color.*—Yellow-Green Group 146B.

Disease resistance: Not known.

REPRODUCTIVE ORGANS

Stamens:

*Anthers.*—1.5–3.0 mm in length.

*Filaments.*—5.0–7.0 mm in length.

*Pollen.*—Golden brown.

Pistils:

*Number.*—1.

*Length.*—5.0–5.5 mm.

*Stigma.*—5–6 parted; Red purple.

*Style.*—2.5–3.0 mm; Red purple.

Ovaries: Superior; pubescent; pale green; 2.5–3.0 mm in length.

Fruit: None observed.

GENERAL CHARACTERISTICS

L'amour' presents a new and distinct color to the geranium industry with pale pink florets accented with a dark pink eye. The light flower color is striking against the medium green foliage. This new geranium variety will please both the grower and the home gardener with its ease of rooting, compact mound habit, basal branching and free and early flowering.

I claim:

1. A new and distinct variety of geranium plant substantially as shown and described.

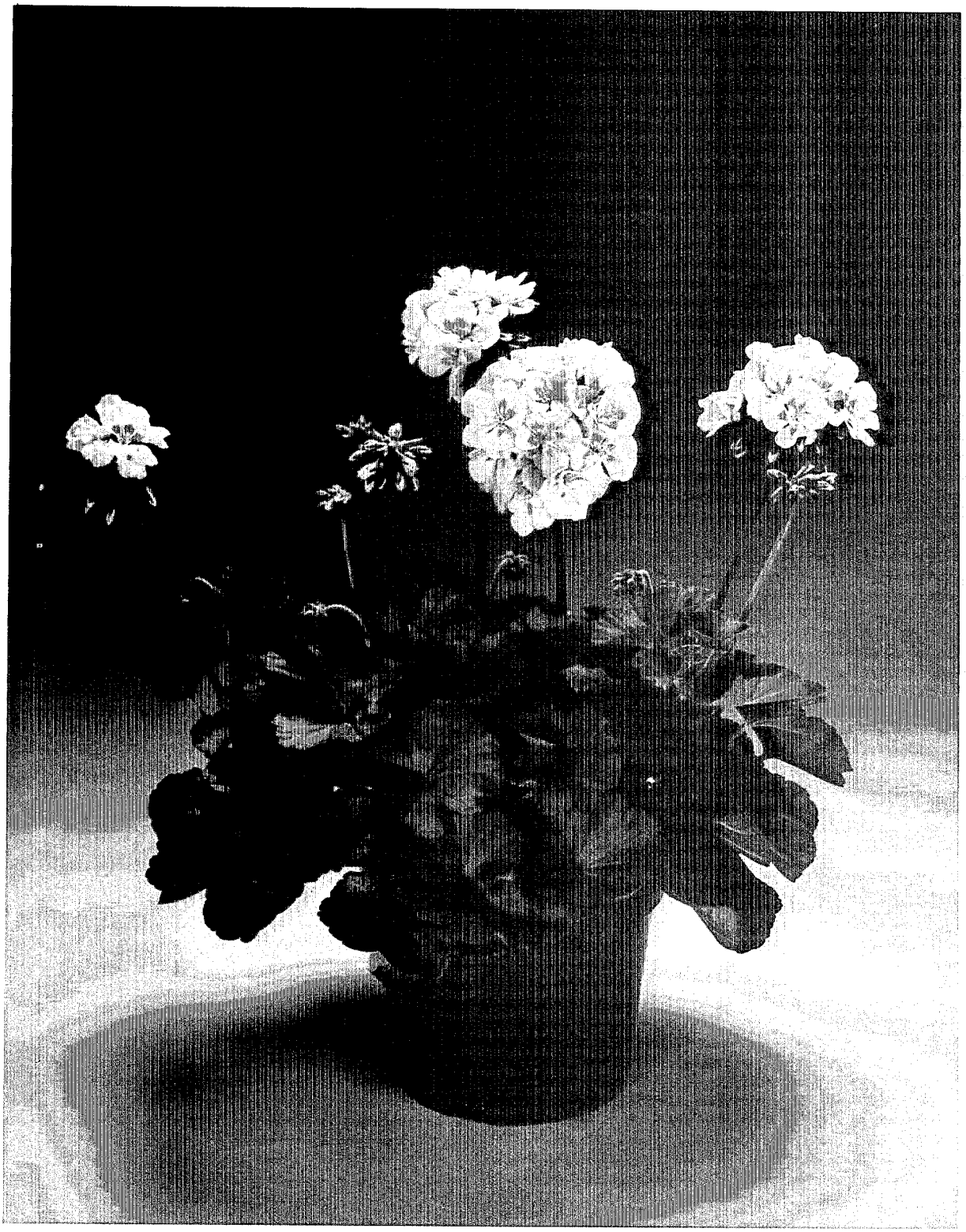

* * * * *